United States Patent [19]

Powell et al.

[11] Patent Number: 5,981,808
[45] Date of Patent: *Nov. 9, 1999

[54] COBALT-CATALYZED PROCESS FOR PREPARING 1, 3-PROPANEDIOL FROM ETYLENE OXIDE

[75] Inventors: Joseph Broun Powell; Lynn Henry Slaugh; David Cleve Eubanks, all of Houston; Stephan Blake Mullin, Katy; Terry Blain Thomason, Houston; Paul Richard Weider, Houston; Thomas Carl Semple, Friendswood, all of Tex.

[73] Assignee: Shell Oil Company, Houston, Tex.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/892,831

[22] Filed: Jul. 15, 1997

Related U.S. Application Data

[63] Continuation of application No. 08/720,270, Sep. 26, 1996, abandoned, which is a continuation of application No. 08/316,676, Sep. 30, 1994, abandoned.

[51] Int. Cl.[6] .................................................. C07C 27/00
[52] U.S. Cl. .......................... 568/862; 568/454; 568/483
[58] Field of Search .................................. 568/454, 483, 568/862

[56] References Cited

U.S. PATENT DOCUMENTS

| | | | |
|---|---|---|---|
| 3,168,553 | 2/1965 | Slaugh | 260/497 |
| 3,456,017 | 7/1969 | Smith | 260/602 |
| 3,463,819 | 8/1969 | Smith | 260/602 |
| 3,687,981 | 8/1972 | Lawrence | 260/340.7 |
| 4,137,240 | 1/1979 | Peterson | 260/340.7 |
| 4,255,279 | 3/1981 | Spohn | 252/413 |
| 4,404,119 | 9/1983 | Lagace | 252/413 |
| 4,873,378 | 10/1989 | Murphy | 568/867 |
| 4,873,379 | 10/1989 | Murphy | 568/867 |
| 4,973,741 | 11/1990 | Beavers | 560/179 |
| 5,030,766 | 7/1991 | Briggs | 568/496 |
| 5,053,562 | 10/1991 | Tau | 568/867 |
| 5,210,318 | 5/1993 | Briggs | 568/496 |
| 5,225,387 | 7/1993 | Briggs | 502/167 |
| 5,256,827 | 10/1993 | Slaugh | 568/454 |
| 5,321,168 | 6/1994 | Roussel | 568/882 |
| 5,504,261 | 4/1996 | Mullin et al. | 568/862 |

OTHER PUBLICATIONS

Falbe, Carbon Monoxide In Organic Synthesis, Springer–Verlag (1970), pp. 14–15.

Falbe, New Synthesis With Carbon Monoxide, Springer–Verlag (1980), p. 131.

*Primary Examiner*—Rebecca Cook

[57] ABSTRACT

1,3-Propanediol is prepared in a process which involves reacting ethylene oxide with carbon monoxide and hydrogen in an essentially non-water-miscible solvent in the presence of a non-phosphine-ligated cobalt catalyst and a catalyst promoter to produce an intermediate product mixture containing 3-hydroxypropanal in an amount less than 15 wt %; extracting the 3-hydroxypropanal from the intermediate product mixture into an aqueous liquid at a temperature less than about 100° C. and separating the aqueous phase containing 3-hydroxypropanal from the organic phase containing cobalt catalyst; hydrogenating the 3-hydroxypropanal in the aqueous phase to 1,3-propanediol; and recovering the 1,3-propanediol.

The process enables the production of 1,3-propanediol in high yield and selectivity without the use of a phosphine ligand-modified cobalt catalyst.

13 Claims, 1 Drawing Sheet

COBALT-CATALYZED PROCESS FOR PREPARING 1, 3-PROPANEDIOL FROM ETYLENE OXIDE

This is a continuation of application Ser. No. 08/720,270, abandoned filed Sep. 26, 1996 which was a continuation of Ser. No. 08/316,676, filed Sep. 30, 1994 abandoned.

BACKGROUND OF THE INVENTION

This invention relates to the preparation of 1,3-propanediol. In one aspect, the invention relates to a cobalt-catalyzed process for manufacturing 1,3-propanediol in high yields without the use of a phosphine ligand for the cobalt catalyst.

1,3-propanediol (PDO) is an intermediate in the production of polyesters for fibers and films. It is known to prepare PDO in a two-step process involving (1) the cobalt-catalyzed hydroformylation (reaction with synthesis gas, $CO/H_2$) of ethylene oxide to intermediate 3-hydroxypropanal (HPA) and (2) hydrogenation of the HPA to PDO. The initial hydroformylation step is carried out at temperatures greater than 100° C. and at high synthesis gas pressure to achieve practical reaction rates. The resulting product mixture is, however, rather unselective for HPA.

In an alternate hydroformylation method, the cobalt catalyst is used in combination with a phosphine ligand to prepare HPA with greater selectivity and at lower temperature and pressure. However, the use of a phosphine ligand adds to the cost of the catalyst and increases the complexity of catalyst recycle.

It would be desirable to prepare HPA in a low-temperature, selective process which did not require the use of a phosphine ligand with the cobalt catalyst.

It is therefore an object of the invention to provide an economic process for the preparation of 1,3-propanediol which does not require the use of a phosphine-ligated catalyst. It is a further object of the invention to provide a cobalt-catalyzed process for the preparation of 1,3-propanediol in which the majority of the cobalt catalyst can be conveniently recycled.

SUMMARY OF THE INVENTION

According to the invention, 1,3-propanediol is prepared in a process comprising the steps of:

(a) contacting, in an essentially non-water-miscible solvent, ethylene oxide with carbon monoxide and hydrogen in the presence of an effective amount of a non-phosphine-ligated cobalt catalyst and an effective amount of a catalyst promoter at a temperature within the range of about 50 to about 100° C. and a pressure within the range of about 500 to about 5000 psig, under conditions effective to produce an intermediate product mixture comprising less than about 15 wt % 3-hydroxypropanal;

(b) adding an aqueous liquid to said intermediate product mixture under carbon monoxide at a pressure within the range of about 20 to about 2000 psig and a temperature less than about 100° C., and extracting into said aqueous liquid a major portion of the 3-hydroxypropanal to provide an aqueous phase comprising 3-hydroxypropanal in greater concentration than the concentration of 3-hydroxypropanal in the intermediate product mixture, and an organic phase comprising a major portion of the cobalt catalyst or a cobalt-containing derivative thereof;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature during at least a portion of the hydrogenation step of at least 40° C. to provide a hydrogenation product mixture comprising 1,3-propanediol;

(e) recovering 1,3-propanediol from the hydrogenation product mixture; and (f) returning at least a portion of the organic phase comprising cobalt catalyst to the process of step (a).

The process enables the production of 1,3-propanediol in high yield and selectivity without the use of a phosphine-ligated cobalt catalyst. The process also enables the recovery and recycle of essentially all of the cobalt catalyst.

DETAILED DESCRIPTION OF THE INVENTION

Figure 1:
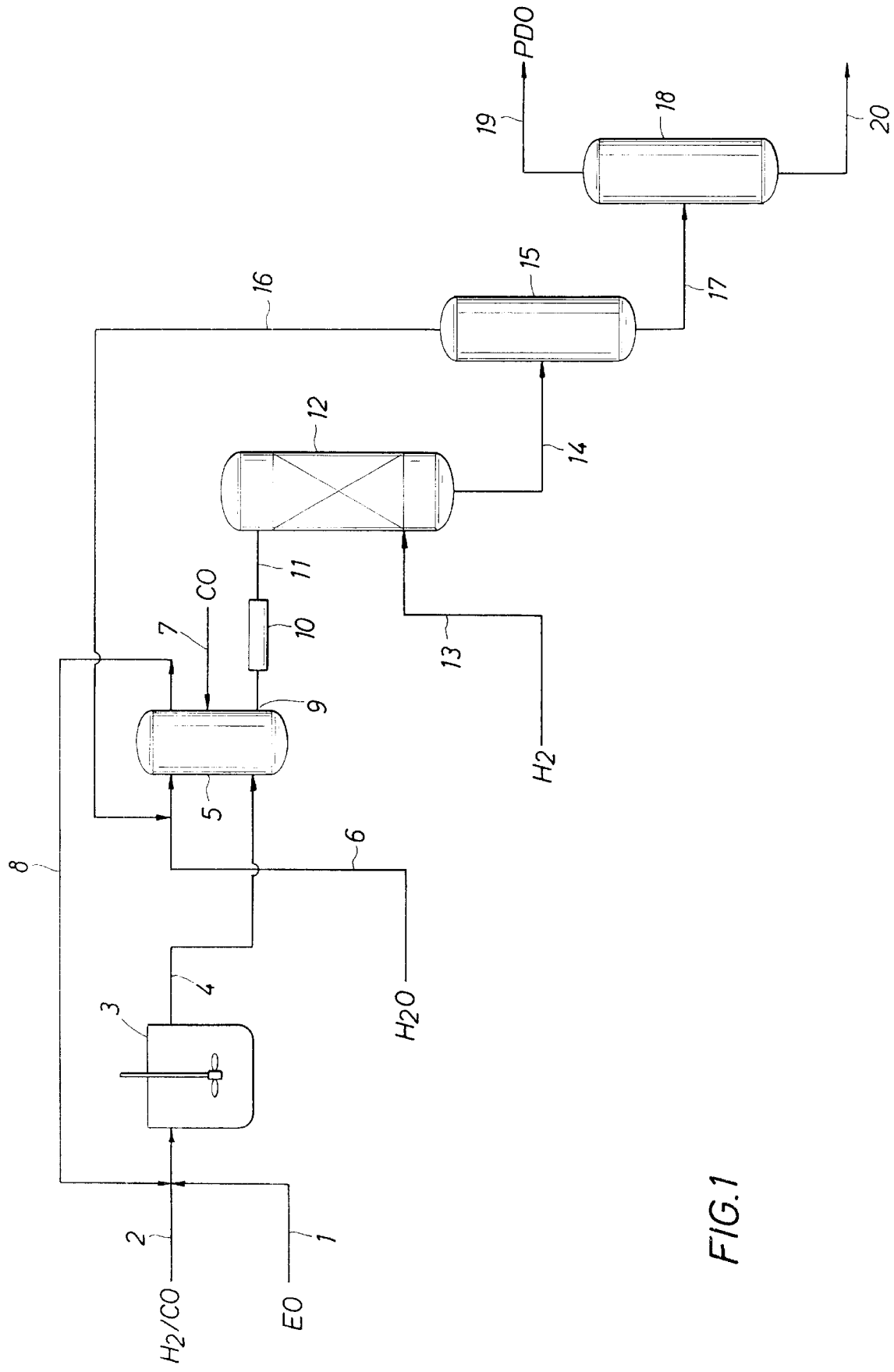
FIG. 1 is a schematic flow diagram of one embodiment of the invention 1,3-propanediol preparation process.

The invention 1,3-propanediol preparation process can be conveniently described by reference to FIG. 1. Separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a non-phosphine-ligated cobalt catalyst, i.e., a cobalt carbonyl which has not been prereacted with a phosphine ligand. The hydrogen and carbon monoxide will generally be introduced into the reaction vessel in a molar ratio within the range of about 1:2 to about 8:1, preferably about 1.5:1 to about 5:1.

The reaction is carried out under conditions effective to produce a hydroformylation reaction mixture comprising a major portion of 3-hydroxypropanal (HPA) and a minor portion of acetaldehyde, while maintaining the level of 3-hydroxypropanal in the reaction mixture at less than 15 wt %, preferably about 5 to about 10 wt %. (To provide for solvents having different densities, the desired concentration of HPA in the reaction mixture can be expressed in molarity, i.e. less than 1.5M, preferably within the range of about 0.5 to about 1M.) Generally, the hydroformylation reaction is carried out at elevated temperature within the range of about 50 to about 100° C., preferably about 60 to about 90° C., most preferably about 75 to about 85° C., and at a pressure within the range of about 500 to about 5000 psig, preferably (for process economics) about 1000 to about 3500 psig, with higher pressures generally imparting greater selectivity. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 100° C.) and relatively short residence times within the range of about 20 minutes to about 1 hour are preferred. In the practice of the invention, it is possible to achieve HPA yields (based on ethylene oxide converted) of greater than 80%, with formation of more than 7 wt % HPA, at rates grater than 30 $h^{-1}$. (Catalytic rates are referred to herein in terms of "turnover frequency" or "TOF" and are expressed in units of moles per mole of cobalt per hour, or $h^{-1}$.) Reported rates are based on the observation that, before a majority of ethylene oxide is converted, the reaction is essentially zero-order in ethylene oxide concentration and proportional to cobalt concentration.

The hydroformylation reaction is carried out in a liquid solvent inert to the reactants. By "inert" is meant that the solvent is not consumed during the course of the reaction. In general, ideal solvents for the phosphine ligand-free process (a) will solubilize carbon monoxide, (b) will exhibit low to moderate polarity such that 3-hydroxypropanal intermediate will be solubilized to the desired concentration of at least about 5 wt % under hydroformylation conditions, and (c) will be essentially non-water-miscible. By "essentially non-water-miscible" is meant that the solvent has a solubility in water at 25° C. of less than 25 wt % so as to form a separate hydrocarbon-rich phase upon water extraction of HPA from the hydroformylation reaction mixture. Preferably this solubility is less than about 10 wt %, most preferably less than about 5 wt %. The solubilization of carbon monoxide in the selected solvent will generally be greater than 0.15 v/v (1 atm, 25° C.), preferably greater than 0.25 v/v, as expressed in terms of Ostwald coefficients.

The preferred class of solvents are alcohols and ethers which can be described according to the formula $$R_2-O-R_1 \quad (1)$$

in which $R_1$ is hydrogen or $C_{1-20}$ linear, branched, cyclic or aromatic hydrocarbyl or mono- or polyalkylene oxide and $R_2$ is $C_{1-20}$ linear, branched, cyclic or aromatic hydrocarbyl, alkoxy or mono- or polyalkylene oxide. The most preferred hydroformylation solvents can be described by the formula $$R_4-\underset{\underset{R_5}{|}}{\overset{\overset{R_3}{|}}{C}}-O-R_1 \quad (2)$$

in which $R_1$ is hydrogen or $C_{1-8}$ hydrocarbyl and mono- or polyalkylene oxide and $R_3$, $R_4$ and $R_5$ are independently selected from $C_{1-8}$ hydrocarbyl, alkoxy and mono- or polyalkylene oxide. Such ethers include, for example, methyl-t-butyl ether, ethyl-t-butyl ether, ethoxyethyl ether, diethyl ether, phenylisobutyl ether, diphenyl ether and diisopropyl ether. Blends of solvents such as tetrahydrofuran/toluene, tetrahydrofuran/heptane and t-butylalcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated cobalt carbonyl compound. Although phosphine-ligated catalysts are active for the described hydroformylation reaction, the invention process is designed to achieve good yield and selectivity without the additional expense of a phosphine ligand. The cobalt catalyst can be supplied to the hydroformylation reactor in essentially any form including metal, supported metal, Raney-cobalt, hydroxide, oxide, carbonate, sulfate, acetylacetonate, salt of a carboxylic acid, or aqueous cobalt salt solution, for example. It may be supplied directly as a cobalt carbonyl such as dicobaltoctacarbonyl or cobalt hydridocarbonyl. If not supplied in the latter forms, operating conditions can be adjusted such that cobalt carbonyls are formed via reaction with $H_2$ and CO, as described in J. Falbe, "Carbon Monoxide in Organic Synthesis," Springer-Verlag, NY (1970). In general, catalyst formation conditions will include a temperature of least 50° C. and a carbon monoxide partial pressure of at least about 100 psig. For more rapid reaction, temperatures of about 120 to 200° C. should be employed, at CO pressures of at least 500 psig. Addition of high surface area activated carbons or zeolites, especially those containing or supporting platinum or palladium metal, is known to accelerate cobalt carbonyl formation from noncarbonyl precursors. The resulting catalyst is maintained under a stabilizing atmosphere of carbon monoxide, which also provides protection against exposure to oxygen. The most economical and preferred catalyst activation and reactivation (of recycled catalyst) method involves preforming the cobalt salt (or derivative) under $H_2/CO$ in the presence of the catalyst promoter employed for hydroformylation. The conversion of $Co^{2+}$ to the desired cobalt carbonyl is carried out at a temperature within the range of about 75 to about 200° C., preferably about 100 to about 140° C. and a pressure within the range of about 1000 to about 5000 psig for a time preferably less than about 3 hours. The preforming step can be carried out in a pressurized preforming reactor or in situ in the hydroformylation reactor.

The amount of cobalt present in the reaction mixture will vary depending upon the other reaction conditions, but will generally fall within the range of about 0.01 wt % to about 1 wt %, preferably about 0.05 to about 0.3 wt %, based on the weight of the reaction mixture.

The hydroformylation reaction is preferably carried out in the presence of a reaction promoter to accelerate the reaction rate. Suitable promoters include sources of mono- and multivalent metal cations of weak bases such as alkali, alkaline earth and rare earth metal salts of carboxylic acids. Also suitable are lipophilic promoters such as lipophilic phosphonium salts and lipophilic amines, which accelerate the rate of hydroformylation without imparting hydrophilicity (water solubility) to the active catalyst. By "lipophilic" is meant that the promoter tends to remain in the organic phase after extraction of HPA with water. The promoter will generally be present in an amount within the range of about 0.01 to about 0.6 moles per mole of cobalt. Suitable lipophilic promoters include tertiary amines such as nonylpyridine and lipophilic phosphonium salts such as tetrabutylphosphonium acetate.

It is generally preferred to regulate the concentration of water in the hydroformylation reaction mixture, as excessive amounts of water reduce [HPA+PDO] selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally being more tolerant of higher water concentrations. For example, optimum water levels for hydroformylation in methyl-t-butyl ether solvent are believed to be within the range of about 1 to about 2.5 wt %.

Following the hydroformylation reaction, the hydroformylation reaction product mixture 4 containing 3-hydroxypropanal, the reaction solvent, 1,3-propanediol, the cobalt catalyst and a minor amount of reaction by-products, is cooled and passed to extraction vessel 5, wherein an aqueous liquid, generally water and optional miscibilizing solvent, are added via 6 for extraction and concentration of the HPA for the subsequent hydrogenation step. Liquid extraction can be effected by any suitable means, such as mixer-settlers, packed or trayed extraction columns, or rotating disk contactors. Extraction can, if desired, be carried out in multiple stages. The water-containing hydroformylation reaction product mixture can be optionally passed to a separate settling tank (not shown) for resolution into aqueous and organic phases. The amount of water added to the hydroformylation reaction product mixture will generally be such as to provide a water:mixture ratio within the range of about 1:1 to about 1:20, preferably about 1:5 to about 1:15. The addition of water at this stage of the reaction may have the additional advantage of suppressing formation of undesirable heavy ends via condensation. Extraction with water provides an aqueous phase which is greater than 20 wt % HPA, preferably greater than 35 wt % HPA, permitting economical hydrogenation of the HPA to PDO and recovery of PDO product. The water extraction is preferably carried out at a temperature within the range of about 25 to about 55° C., with higher temperatures avoided because of the tendency to promote heavy ends formation or catalyst disproportionation to inactive, water-soluble cobalt species.

According to the invention and in order to maximize catalyst recovery, the water extraction is carried out under carbon monoxide. The carbon monoxide can be introduced into the extraction vessel e.g. via 7, or the extraction can be carried out under residual carbon monoxide from the hydroformylation reaction, generally under a carbon monoxide partial pressure less than that maintained for hydroformylation. Extraction of HPA under carbon monoxide enables 80% or more of the cobalt catalyst to be extracted into the organic phase and subsequently recycled to the hydroformylation reaction via solvent recycle. The partial pressure of carbon monoxide is preferably maintained within the range of about 20 to about 2000 psig, most preferably about 50 to about 500 psig. The carbon monoxide may be combined with hydrogen or another inert gas such as nitrogen, methane or argon.

The preferred catalyst recovery process begins with the above-described water extraction of HPA from the hydroformylation product mixture. The majority of the cobalt catalyst will remain in the organic phase, with 1–20% of the cobalt catalyst passing into the water phase. The catalyst-containing organic phase can be recycled via 8 to the hydroformylation reactor, with optional purge of heavy ends. Aqueous extract 9 is optionally passed through one or more acid ion exchange resin beds 10 for removal of any cobalt catalyst present, and the decobalted aqueous product mixture 11 is passed to hydrogenation vessel 12 and reacted with hydrogen 13 in the presence of a hydrogenation catalyst to produce a hydrogenation product mixture 14 containing 1,3-propanediol. The hydrogenation step may also revert some heavy ends to PDO. The solvent and extractant water 16 can be recovered by distillation and recycled to the water extraction process via a further distillation (not shown) for separation and purge of light ends. PDO-containing stream 17 can be passed to distillation column 18 for separation of PDO 19 from heavy ends 20.

Hydrogenation of the HPA to PDO can be carried out in aqueous solution at an elevated temperature of at least about 40° C., generally within the range of about 50 to about 175° C., under a hydrogen pressure of at least about 100 psig, generally within the range of about 200 to about 2000 psig. The reaction is carried out in the presence of a hydrogenation catalyst such as any of those based upon Group VIII metals, including nickel, cobalt, ruthenium, platinum and palladium, as well as copper, zinc and chromium and mixtures or alloys thereof. Nickel catalysts, including bulk, supported and fixed-bed forms, provide acceptable activities and selectivities at moderate cost. Highest yields are achieved under slightly acidic reaction conditions.

Commercial operation will require efficient cobalt catalyst recovery with essentially complete recycle of cobalt to the hydroformylation reaction. The preferred catalyst recovery process begins with the above-described water extraction of HPA from the hydroformylation product mixture. A major portion of the cobalt catalyst will remain in the organic solvent phase, with the remaining cobalt catalyst passing into the water phase. The organic phase can be recycled to the hydroformylation reactor, with optional purge of heavy ends. Optionally, further decobalting of catalyst in the water layer can be effected by any suitable method, such as complete or partial oxidation of cobalt followed by precipitation and filtration, distillation, deposition on a solid support, or extraction using a suitable extractant, preferably prior to final cobalt removal by ion exchange (10).

In the preferred method of catalyst recovery from the aqueous phase, the catalyst-containing liquid is passed to a pressure vessel (not shown) for oxidation of the water-soluble cobalt compound to an organic-soluble cobalt carbonyl species (principally dicobaltoctacarbonyl) from which active catalyst is readily derived under hydroformylation conditions. The oxidation is most efficiently carried out by addition of air or $O_2$ under a carbon monoxide atmosphere, optionally in the presence of a carboxylic acid. The reaction will generally be carried out at a temperature within the range of about 25 to about 55° C. and at pressures within the range of about 50 to about 200 psig carbon monoxide, optionally with additional gaseous diluents such as nitrogen to maintain a nonflammable gaseous mixture relative to the amount of oxygen added.

The invention process permits the selective and economic synthesis of PDO at moderate temperatures and pressures without the use of a phosphine ligand for the hydroformylation catalyst. The process involves preparation of a reaction product mixture dilute in intermediate HPA, then concentration of this HPA by water extraction followed by hydrogenation of the aqueous HPA to PDO.

EXAMPLE 1

This example illustrates cobalt catalyst recovery under a nitrogen atmosphere during water extraction of HPA from a hydroformylation reaction product mixture. 13 g of ethylene oxide were hydroformylated at 80° C. under 1500 psig of 2.3:1 $H_2$/CO, in an unpromoted reaction mixture containing 0.87 g dicobaltoctacarbonyl, 1.5 g toluene (marker) and 147.5 g methyl-t-butyl ether solvent. After 5.75 hours of reaction, 4.7 wt % HPA was observed in solution. The reaction mixture was cooled to 25° C. and extracted under nitrogen with 30 g of deionized water. 70.56 g of the upper solvent layer containing 901 ppm cobalt and 31.85 g of the lower aqueous layer containing 1828 ppm cobalt were isolated. Thus, 52% of the cobalt remained with the organic layer following water extraction.

After removal of the organic layer from the reaction, 0.43 g of a 36% acetic acid/water solution were added to the lower aqueous layer along with 150 ml ambient pressure air and a 100 psig nitrogen blanket. The mixture was stirred for 30 min. at room temperature, to attempt to oxidize $Co^{-1}$, present as tetracarbonyl anion, to dicobaltoctacarbonyl. The resulting oxidation reaction mixture was treated with 26.9 g of fresh methyl-t-butyl ether to extract any oil-soluble dicobaltoctacarbonyl. No cobalt was extracted into the ether phase.

EXAMPLE 2

This example illustrates cobalt catalyst recovery under a carbon monoxide atmosphere during water extraction of HPA from a promoted hydroformylation reaction product mixture. 10 g of ethylene oxide were hydroformylated in a reaction mixture containing 0.87 g dicobaltoctacarbonyl, 0.14 g sodium acetate trihydrate promoter, 1.5 g toluene (marker), 1.5 g undecanol (marker) and 146 g methyl-t-butyl ether (MTBE) at 80° C. and 1500 psig of 2.3:1 $H_2/CO$. Analysis after 2 hours 12 minutes of reaction indicated 7.9 wt % HPA in the reaction product mixture.

After removal of a large fraction of this reaction mixture for alternate studies, 51 g of the remaining reaction mixture were placed in the reactor and cooled to 27° C. The reactor was vented and recharged with 200 psig of CO. 16 g of water were added to extract HPA. After transferring a majority of the mixture to a phase separator under 200 psig carbon monoxide, 41.2 g of upper organic layer were isolated and found to contain 1893 ppm cobalt. 12.9 g of the aqueous layer contained 1723 ppm cobalt. 78% of the cobalt present was thus present in the organic layer. The lower aqueous layer was re-extracted under nitrogen with 1 part fresh MTBE. No cobalt appeared in the organic layer following the attempted extraction.

0.2 g of 36% acetic acid in water were then added to the lower aqueous layer/MTBE mixture. A small amount of air was introduced to oxidize the remaining cobalt catalyst under a blanket of nitrogen. 23% of the remaining cobalt partitioned into the organic layer. Total cobalt recovery (initial water extraction plus partial oxidation and extraction) of cobalt was 83%. The organic layer was found to contain 0.9 wt % HPA, while the aqueous layer contained about 21.4 wt % HPA.

As can be seen by comparison of this result with Example 1, water extraction of HPA under CO significantly improved cobalt recycle in the organic layer. Moreover, some of the cobalt remaining in the aqueous phase could be recovered by partial oxidation and extraction with MTBE.

EXAMPLE 3

This example further illustrates the use of a carbon monoxide atmosphere to improve catalyst recovery for recycle after hydroformylation. 14 g of ethylene oxide were hydroformylated with 0.87 g dicobaltoctacarbonyl, 0.14 g of sodium acetate trihydrate, 1.5 g toluene, 1.5 g undecanol, 4.5 g tetrahydrofuran and 146 g MTBE, under 1500 psig 3:1 $H_2/CO$ at 80° C. After 1.5 hr, the reaction mixture was found to contain 8.31 wt % HPA.

The reaction mixture was cooled to room temperature and extracted with 30 g of deionized water under an atmosphere of 200 psig CO. 72.2 g of an upper organic layer containing 1638 ppmw cobalt were isolated. 33.4 g of a lower aqueous layer containing 1040 ppmw cobalt. Cobalt recycle with the organic layer was 77%.

0.2 g of 36% acetic acid in water were added to the lower layer, along with 30 g of fresh MTBE solvent, 150 ml of ambient pressure air and 850 psig CO. The mixture was stirred for 30 min. at 25° C. and then the phases were allowed to separate. 29.3 g of upper organic layer containing 1158 ppmw cobalt were recovered. 32.1 g of lower aqueous layer contained only 123 ppmw cobalt. Overall, 98% of the starting cobalt catalyst was recovered and recycled with MTBE solvent to the hydroformylation reaction.

EXAMPLE 4

A series of experiments was done to determine the effect of extraction under carbon monoxide, alone or as a $CO/H_2$ blend, on the recovery of cobalt following hydroformylation. Hydroformylations employed sodium acetate promoter in MTBE solvent under essentially the same reaction conditions as described previously.

Extraction conditions and results are shown in Table 1. As can be seen from the table, extraction under CO increased cobalt recycle in the organic layer following water extraction.

TABLE 1

| Gas | Ex-traction psig | Extraction Temp. (° C.) | wtOL wt AL | OL Co (ppm) | AL Co (ppm) | % Co Recycle* |
|---|---|---|---|---|---|---|
| $N_2$ | 1 | 80 | 2.5 | 0 | 5900 | 0 |
| $N_2$ | 100 | 25 | 4.97 | 913 | 5400 | 46 |
| $N_2$ | 1 | 25 | 0.76 | 795 | 444 | 58 |
| $N_2$ | 100 | 25 | 2.22 | 901 | 1828 | 52 |
| 1:1 $H_2/CO$ | approx. 5 | 25 | 5.91 | 1664 | 1989 | 83 |
| CO | 100 | 25 | 2.24 | 433 | 368 | 73 |
| CO | 200 | 25 | 3.19 | 1893 | 1723 | 78 |
| CO | 200 | 25 | 1.85 | 2235 | 416 | 91 |
| CO | 300 | 25 | 2.16 | 1658 | 1040 | 77 |

OL = organic layer
AL = aqueous layer
*Percent total cobalt retained in organic layer.

EXAMPLE 5

A series of experiments was done to determine the effect of extraction under carbon monoxide on the recovery of cobalt following hydroformylation. Hydroformylations were conducted on 300-ml or 1-gallon scales in the presence of quaternary ammonium acetate (Ethoquad® 2 C/11) promoter (0.1 moles, relative to cobalt) at 80° C. in MTBE solvent, and 2.3:1 to 3.0:1 $H_2/CO$ (with total pressures given in Table 2). Reactions were restricted to formation of less than 10 wt % HPA prior to water extraction. Water extractions were carried out at 25–40° C. and 50–300 psig CO, with varying amounts of water added to give organic/aqueous phase ratios of 1.5:1 to 4:1. As can be seen from Table 2, the use of a lipophilic ammonium salt promoter and extraction under CO enabled the recycle of 90% or more of the cobalt catalyst with the hydroformylation reaction solvent, while HPA was preferentially concentrated and extracted into the aqueous phase at a greater than 10:1 ratio. Thus, cobalt catalyst and HPA were efficiently separated. Moveover, Run 7 represented a recycle of catalyst from Run 6 (1-gallon scale). For Run 7, a hydroformylation rate of 33 $h^{-1}$ was obtained, compared with a rate of 35 $h^{-1}$ in Run 6. This illustrates that the invention enables the majority of the catalyst to be recycled in essentially active form.

TABLE 2

| Run | Hydrof. psig | Recycle # | % Co Recycled OL | HPA wt % AL | HPA wt % OL |
|---|---|---|---|---|---|
| 1 | 1500 | 0 | 91.4 | 12.1 | 1.1 |
| 2 | 1500 | 0 | 91.5 | 20.3 | 0.9 |
| 3 | 1500 | 0 | 90.4 | 21.7 | 1.2 |
| 4 | 1500 | 0 | 94.4 | 23.2 | 0.8 |
| 5 | 1500 | 1 | 81.5 | 17.7 | 1.4 |
| 6 | 2750 | 0 | 99.2 | 22.7 | 0.7 |
| 7 | 2750 | 1 | 92.1 | 24.8 | 1.6 |

We claim:

1. A process for preparing 1,3-propanediol comprising the steps of:

(a) contacting, in an essentially non-water-miscible solvent, ethylene oxide with carbon monoxide and hydrogen in the presence of a catalytic amount of a non-phosphine-ligated cobalt compound and an effective amount of a catalyst promoter at a temperature within the range of about 50 to about 100° C. and a pressure within the range of about 500 to about 5000 psig, under reaction conditions effective to produce an intermediate product mixture comprising less than 15 wt % 3-hydroxypropanal:

(b) adding an aqueous liquid to said intermediate product mixture under a carbon monoxide pressure within the range of about 20 to about 2000 psig, and extracting into said aqueous liquid a major portion of the 3-hydroxypropanal at a temperature less than about 100° C. to provide an aqueous phase comprising 3-hydroxypropanal in greater concentration than the concentration of 3-hydroxypropanal in the intermediate product mixture, and an organic phase comprising a major portion of the cobalt compound or a cobalt-containing derivative thereof;

(c) separating the aqueous phase from the organic phase;

(d) contacting the aqueous phase comprising 3-hydroxypropanal with hydrogen in the presence of a hydrogenation catalyst at a pressure of at least about 200 psig and a temperature during at least a portion of the hydrogenation step of at least about 40° C. to provide a hydrogenation product mixture comprising 1,3-propanediol;

(e) recovering 1,3-propanediol from the hydrogenation product mixture; and (f) returning at least a portion of the organic phase comprising cobalt compound to the process of step (a).

2. The process of claim 1 in which the carbon monoxide atmosphere pressure of step (b) is maintained within the range of about 50 to about 500 psig.

3. The process of claim 1 in which the carbon monoxide of step (b) is combined with a gas selected from the group consisting of argon, hydrogen, nitrogen and methane.

4. The process of claim 1 in which the extraction of step (c) is carried out at a temperature within the range of about 25 to about 55° C.

5. The process of claim 1 in which the concentration of 3-hydroxypropanal in the aqueous phase is greater than about 20 wt %.

6. The process of claim 1 in which the concentration of 3-hydroxypropanal in the aqueous phase is greater than about 35 wt %.

7. The process of claim 1 in which the aqueous liquid of step (c) is water.

8. The process of claim 1 in which essentially all the cobalt compound remaining in the aqueous phase after step (c) is removed from the aqueous phase prior to step (d).

9. The process of claim 1 in which step (a) is carried out in the presence of about 1 to about 2.5 wt % water.

10. The process of claim 9 in which the organic solvent is methyl-t-butyl ether.

11. The process of claim 1 in which at least about 80 wt % of the cobalt present in step (a) is extracted into the organic phase in step (b).

12. A process of preparing 1,3-propanediol comprising the steps of:

(a) contacting, in a solvent comprising an ether, ethylene oxide with carbon monoxide and hydrogen in the presence of a catalytic amount of a non-phosphine-ligated cobalt compound, at a temperature within the range of about 60 to about 90° C. and a pressure within the range of about 1000 to about 3500 psig, under reaction conditions effective to produce an intermediate product mixture comprising about 5 to about 10 wt % 3-hydroxypropanal;

(b) adding an aqueous liquid to said intermediate product mixture under a carbon monoxide atmosphere at a pressure within the range of about 50 to about 500 psig, and extracting into said aqueous liquid a major portion of the 3-hydroxypropanal at a temperature within the range of about 25 to about 55° C. to provide an aqueous phase comprising 3-hydroxypropanal in greater concentration than the concentration of 3-hydroxypropanal in the intermediate product mixture, and an organic phase comprising at least about 80 wt % of the cobalt compound or a derivative thereof;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature during at least a portion of the hydrogenation step of at least about 40° C. to provide a hydrogenation product mixture comprising 1,3-propanediol;

(e) recovering 1,3-propanediol from the hydrogenation product mixture; and (f) returning at least a portion of the organic phase comprising cobalt compound to the process of step (a).

13. The process of claim 12 in which the carbon monoxide of step (b) is combined with a gas selected from the group consisting of argon, hydrogen, nitrogen and methane.

* * * * *